United States Patent
Ho et al.

(10) Patent No.: US 9,322,778 B2
(45) Date of Patent: Apr. 26, 2016

(54) OPTICAL SENSING APPARATUS AND A METHOD FOR DETECTING CHARACTERISTICS OF A SAMPLE

(71) Applicants: The Chinese University of Hong Kong, Hong Kong (CN); City University of Hong Kong, Hong Kong (CN)

(72) Inventors: Ho Pui Ho, Hong Kong (CN); Shu Yuen Wu, Hong Kong (CN); Chi-Man Lawrence Wu, Hong Kong (CN); Siu Pang Ng, Hong Kong (CN); Siu Kai Kong, Hong Kong (CN)

(73) Assignees: THE CHINESE UNIVERSITY OF HONG KONG, Hong Kong (CN); CITY UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 14/694,098

(22) Filed: Apr. 23, 2015

(65) Prior Publication Data
US 2015/0308950 A1 Oct. 29, 2015

Related U.S. Application Data

(60) Provisional application No. 61/983,211, filed on Apr. 23, 2014.

(51) Int. Cl.
*G01B 9/02* (2006.01)
*G01N 21/552* (2014.01)
*G01N 21/45* (2006.01)

(52) U.S. Cl.
CPC .............. *G01N 21/553* (2013.01); *G01N 21/45* (2013.01); *G01N 2201/0683* (2013.01)

(58) Field of Classification Search
CPC ...... G01B 9/02; G01J 9/02; G01J 2009/0261; G01J 4/04; G01N 21/45
USPC ......................................................... 356/491
See application file for complete search history.

(56) References Cited

U.S. PATENT DOCUMENTS

| | | | | |
|---|---|---|---|---|
| 6,493,097 B1 * | 12/2002 | Ivarsson | ............. | G01B 11/0625 356/630 |
| 7,336,359 B1 * | 2/2008 | Simpson | ............... | G01N 21/211 356/364 |
| 8,488,120 B2 * | 7/2013 | Hall | ........................ | G01N 21/21 356/369 |
| 2003/0067612 A1 * | 4/2003 | Ivarsson | ............. | G01B 11/0625 356/600 |
| 2009/0086210 A1 * | 4/2009 | Ho | ........................ | G01N 21/553 356/445 |
| 2013/0329230 A1 * | 12/2013 | Wu | ........................ | G01N 21/553 356/491 |

\* cited by examiner

*Primary Examiner* — Tarifur Chowdhury
*Assistant Examiner* — MD M Rahman
(74) *Attorney, Agent, or Firm* — Knobbe Martens Olson & Bear LLP (57) ABSTRACT

An optical sensing apparatus and a method for detecting characteristics of a sample.

20 Claims, 6 Drawing Sheets

OPTICAL SENSING APPARATUS AND A METHOD FOR DETECTING CHARACTERISTICS OF A SAMPLE

RELATED APPLICATIONS

This application claims priority to U.S. Provisional Patent Application No. 61/983,211, filed Apr. 23, 2014, the content of which is incorporated herein by reference.

TECHNICAL FIELD

The present application relates to an optical sensing apparatus and a method for detecting characteristics of a sample.

BACKGROUND

Over three decades of development, surface plasmon resonance (SPR) technology has become a standard technology for label-free characterization of bimolecular interactions. One of the its advantage is that the SPR sensors can provide real-time quantitative measurement by observing amplitude, angular reflectivity, spectral absorption dip or corresponding phase shift of the SPR influenced light (Ann. Phys. (berlin), 524, 637-662, 2012). Recent research efforts have been focused on the development of a SPR sensor with a wide dynamic range and a high sensitivity.

Several so-called wide dynamic range phase SPR sensors have been developed. U.S. Pat. No. 7,027,676 by Van Wiggeren et al. proposed a method to replace the Zeman's laser on optical heterodyne phase detection scheme by using an optical polarization delay unit and tunable laser. As it scans across a range of frequencies of the light source, a frequency offset between the p- and s-polarized light occurs. A modulated optical detection signal can be produced by interference of the p- and s-polarized light. U.S. Pat. No. 8,169,617 by Ho et al. proposed a new design combining phase detection and angular interrogation to simultaneously achieve high sensitivity and a wide dynamic range.

Later, U.S. Ser. No. 13/113,837 by Wu et al. proposed a white light SPR interferometry scheme to achieve both high sensitivity and wide dynamic range via a different mechanism. In their setup, a Michelson interferometer is employed as a phase detecting unit on both p- and s-polarized light. In essence, the design has two interferometers operating independently on the p-polarization and s-polarization components with identical paths. With the SPR sensor head incorporated to one arm of the interferometer, the researchers have achieve differential SPR phase detection by measuring the phase of the p-polarized and s-polarized light separately using a polarization separating Wollaston prism. Since the SPR effect only affects the p-polarization while leaves the s-polarization unchanged, simple subtraction between the phase values measured from the two polarizations will yield a true SPR phase, which is free from any unwanted signals caused by environmental fluctuations or the system itself.

SUMMARY

The present application proposes an optical sensing apparatus and a solution for detecting characteristics of a sample.

According to an embodiment of the present application, disclosed is an optical sensing apparatus. It may comprise a broadband source, an interferometer, a reference device, a SPR sensor and a determiner. The broadband source is configured to generate a first light beam containing p-polarized and s-polarized components. The interferometer is configured to direct the p-polarized and s-polarized components to a first path and a second path, respectively. The first path has different length from the second path such that the p-polarized and s-polarized components are reflected and then recombined to provide a second light beam with interference between the p-polarized and s-polarized components. The reference device is configured to receive a part of the second light beam to extract a reference optical characteristic variation induced by the interference between the p-polarized and s-polarized components of the second light beam. The SPR sensor is configured to receive the other part of the second light beam and to introduce a SPR effect associated with a sample to the second light beam, such that a third light beam with a probe optical characteristic variation induced by the SPR effect is generated. The determiner unit is configured to receive the third light beam to extract the probe optical characteristic variation induced by the SPR effect and to determine characteristics of the sample by comparing the reference optical characteristic variation and the probe optical characteristic variation.

According to a further embodiment of the present application, disclosed is a method for detecting characteristics of a sample. The method may comprise: generating, from a broadband source, a first light beam containing p-polarized and s-polarized components; directing the p-polarized and s-polarized components to a first path and a second path, respectively, wherein the first path has different length from the second path such that the p-polarized and s-polarized components are reflected and then recombined to provide a second light beam with a interference between the p-polarized and s-polarized components; extracting a reference optical characteristic variation induced by the interference between the p-polarized and s-polarized components of a part of the second light beam; introducing a SPR effect associated with a sample to the other part of the second light beam, such that a third light beam with a probe optical characteristic variation induced by the SPR effect is generated; extracting the probe optical characteristic variation induced by the SPR effect of the third light beam; and comparing the reference optical characteristic variation and the probe optical characteristic variation to determine characteristics of the sample.

BRIEF DESCRIPTION OF THE DRAWING

Exemplary non-limiting embodiments of the invention are described below with reference to the attached figures. The drawings are illustrative and generally not to an exact scale.

DETAILED DESCRIPTION

Reference will now be made in detail to exemplary embodiments, examples of which are illustrated in the accompanying drawings. When appropriate, the same reference numbers are used throughout the drawings to refer to the same or like parts.

Figure 1:
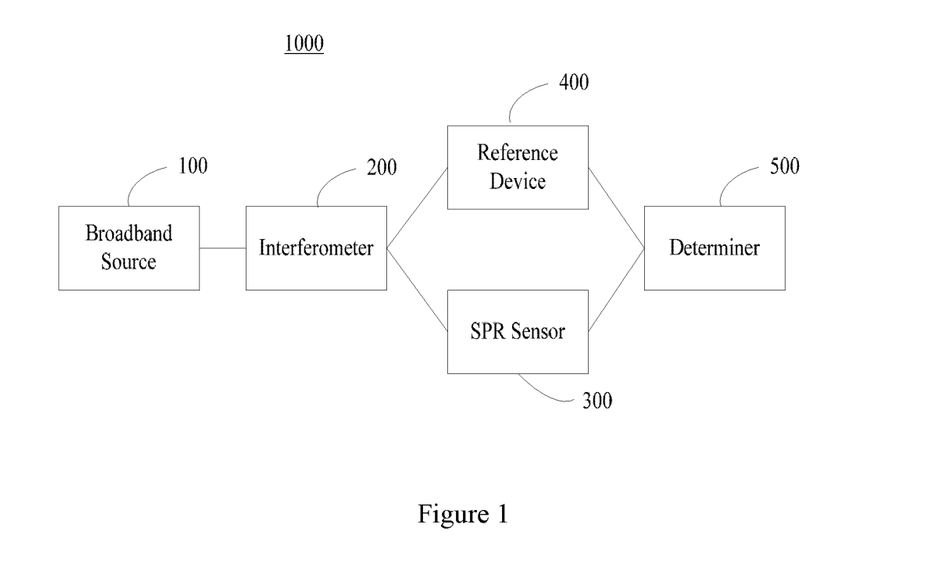
FIG. 1 is a schematic diagram illustrating an optical sensing apparatus consistent with some disclosed embodiments.

FIG. 1 is a schematic diagram illustrating an optical sensing apparatus 1000 consistent with some disclosed embodiments. As shown in FIG. 1, the apparatus 1000 may comprise a broadband source 100, an interferometer 200, a SPR sensor 300, a reference device 400 and a determiner 500.

According to an embodiment, the broadband source 100 may be configured to generate a first light beam containing p-polarized and s-polarized components. In an another embodiment, the broadband source 100 may be produced by cascading more than one single-wavelength light source or multi-wavelength light source, such as gas laser, solid state laser, laser diode, light emitting diode and any other suitable electromagnetic radiation source. The electromagnetic radiation may be visible light, visible to infrared light, infrared light, ultraviolet light or ultraviolet to visible light.

According to an embodiment, the interferometer 200 may be configured to direct the p-polarized and s-polarized components to a first path and a second path, respectively. The first path has different length from the second path such that the p-polarized and s-polarized components are reflected and then recombined to provide a second light beam with a interference between the p-polarized and s-polarized components. The interferometer 200 may be a Michelson interferometer, Mach-Zehnder interferometer or any other suitable interferometer.

In an embodiment, the reference device 400 may be configured to receive a part of the second light beam to extract a reference optical characteristic variation induced by the interference between the p-polarized and s-polarized components of the second light beam. The SPR sensor 300 may be configured to receive the other part of the second light beam and to introduce a SPR effect associated with a sample to the second light beam, such that a third light beam with a probe optical characteristic variation induced by the SPR effect is generated. The determiner 500 may be configured to receive the third light beam to extract the probe optical characteristic variation induced by the SPR effect and to compare the reference optical characteristic variation and the probe optical characteristic variation in order to determine characteristics of the sample.

In the application, the use of broadband light source and interferometer can provide wide dynamic range on SPR spectral and spectral phase with high sensitivity. It also can provide relatively simple optical configuration compared to the previous SPR biosensor.

Figure 2:
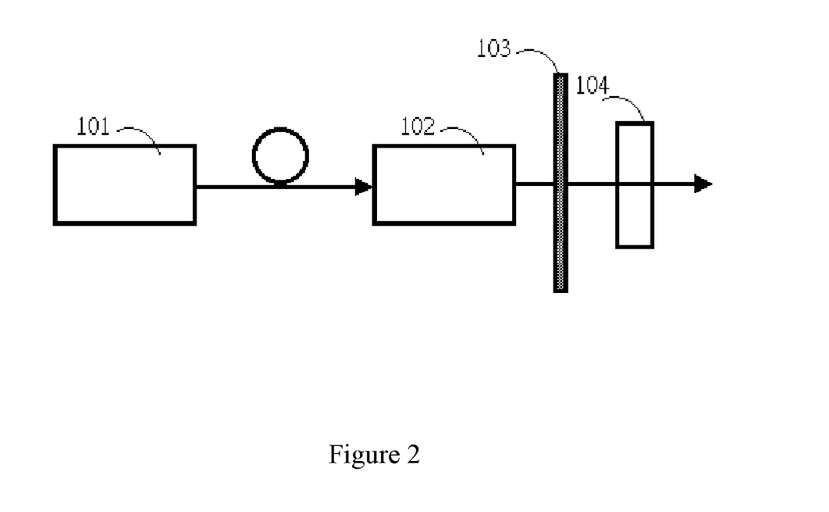
FIG. 2 is a schematic diagram illustrating a broadband source consistent with some disclosed embodiments.

FIG. 2 is a schematic diagram illustrating a broadband source 100 consistent with some disclosed embodiments. As shown in FIG. 2, the broadband source 100 may comprise a broadband electromagnetic radiation source 101, a collimator 102, a polarizer 103 and a variable optical iris 104.

In the embodiment, the broadband electromagnetic radiation source 101 may be configured to emit a broadband light beam containing the p-polarized and s-polarized components. Alternatively or additionally, the broadband electromagnetic radiation source 101 may be a multi-wavelength electromagnetic radiation source, such as a light emitting diode (LED), a tungsten lamp, a halogen lamp, an arc discharge lamp, a super luminescent diode (SLD), a fluorescence tube, a super continuum laser and any other suitable multi-wavelength electromagnetic radiation source. For example, a solid state WLED with a rated electrical power of 3 Watt (for example) is employed and its polarization is regarded as random.

The collimator 102 may be configured to convert the broadband light beam into a parallel light beam. Alternatively or additionally, the collimator 102 may be a lens system or a field of view confinement system. The polarizer 103 may be configured to select a content ratio between the p-polarized and s-polarized components by varying the angle of its polarization axis. The content ratio between p- and s-polarization components may be set at 50:50. This means that the polarization angle of the polarizer is 45° from the axis of the s-polarization. In addition, the variable optical iris 104 is configured to adjust a beam diameter of the light beam and to restrict the angular field of view of the light beam.

Figure 3:
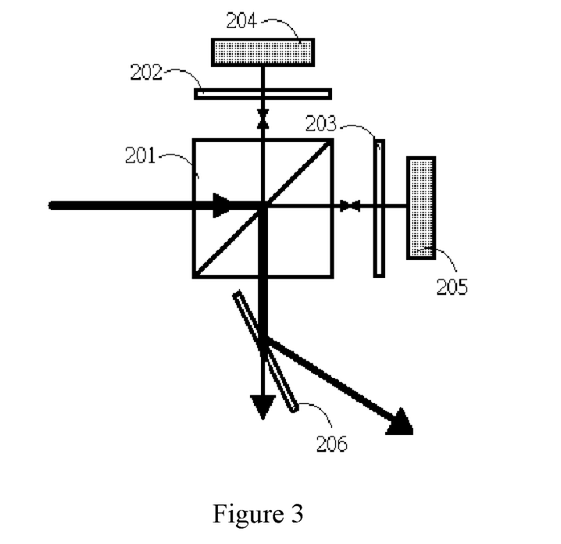
FIG. 3 is a schematic diagram illustrating an interferometer consistent with some disclosed embodiments.

As shown in FIG. 3, the interferometer 200 may comprise a broadband polarizing beam splitter 201, first and second quarter chromatic waveplates 202 and 203, first and second reflective units 204 and 205. In an embodiment, the broadband polarizing beam splitter 201 may be configured to split the first light beam into the p-polarized light beam passing a first path and the s-polarized component light beam passing a second path. According to the embodiment, the s-polarization component is reflected by 90 degree and the p-polarization component is directly transmitted. The first quarter chromatic waveplate 202 in the first path located between the broadband polarizing beam splitter 201 and first reflective unit 204 to change the polarization of the passing light beam. The result is that the polarization of the light beam is changed from s-polarization to p-polarization when the light beam passes through the first quarter chromatic waveplate 202 back and forth. The first reflective unit 204 may be configured to reflect the light beam passing the first path.

Similarly, the second quarter chromatic waveplate 203 in the second path located between the broadband polarizing beam splitter 201 and second reflective unit 205 to change the polarization of the passing light beam. The result is that the polarization of the light beam is changed from p-polarization to s-polarization when the light beam passes through the second quarter chromatic waveplate 203 back and forth. The second reflective unit 205 may be configured to reflect the light beam passing the second path. The reflective units 204 and 205 may be high precision surface flatness reflective mirrors and positioned to introduce sufficient optical path different between the two paths and suitable optical alignment to ensure efficient interference between the p- and s-polarization components.

Then the reflected light beams are recombined by the broadband polarizing beam splitter 201, such that interference between the p-polarized and s-polarized components is generated. In addition, the interferometer 200 may further comprise a non-polarizing beam splitter 206, and the reflected light beam may pass through the broadband polarizing beam splitter 201 to the non-polarizing beam splitter 206. The non-polarizing beam splitter 206 may be configured to separate the recombined light beam into two parts. For example, one part, which is only 5% of the total intensity, is for a reference beam to go to reference device 400 and the other is for a probe beam to go to the SPR sensor 300. This configuration can avoid the light beam reflected back to the broadband source 100 along the opposite path.

Figure 4:
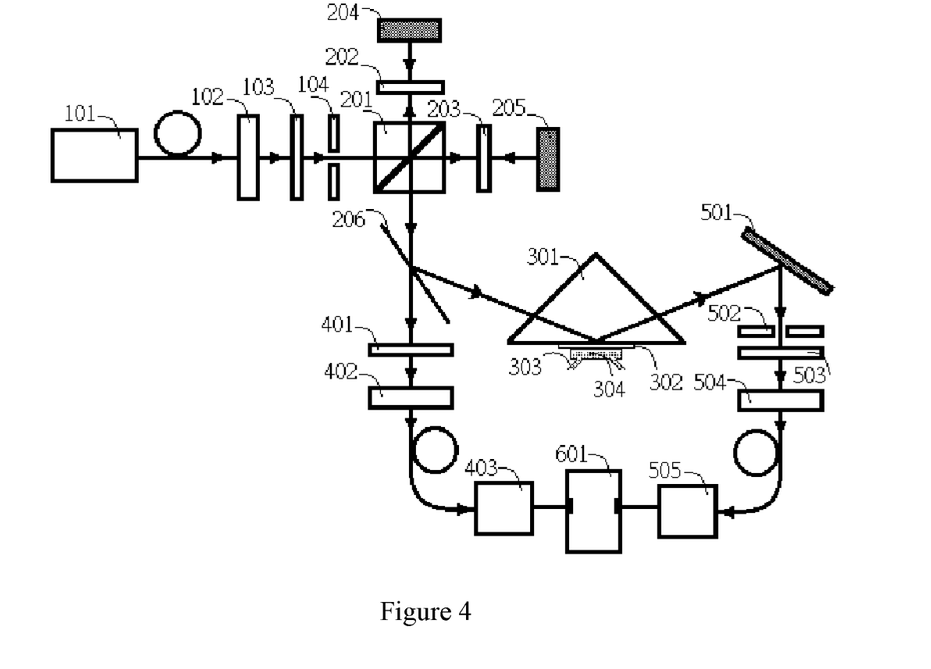
FIG. 4 is a structural schematic diagram illustrating an optical sensing apparatus consistent with some disclosed embodiments.
Figure 7:
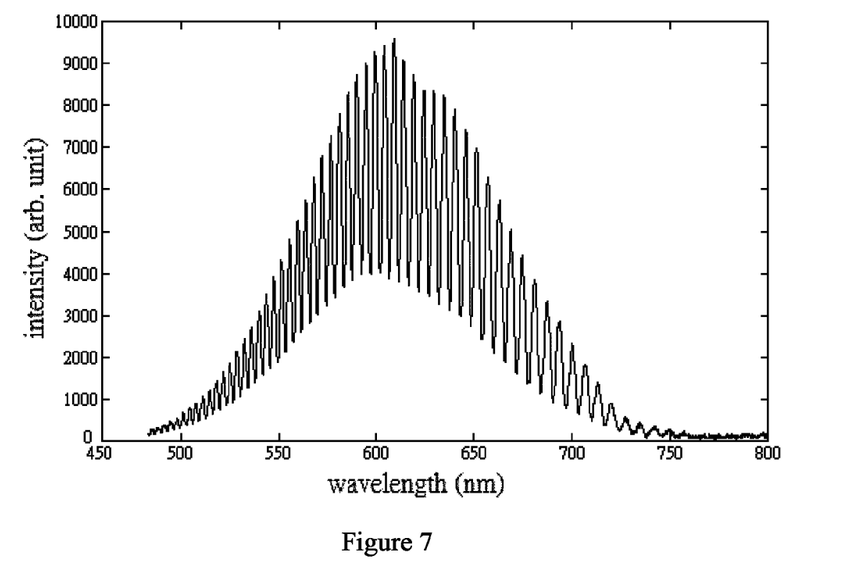
FIG. 7 is a graph illustrating a raw signal of the reference device according to some disclosed embodiments.
Figure 8:
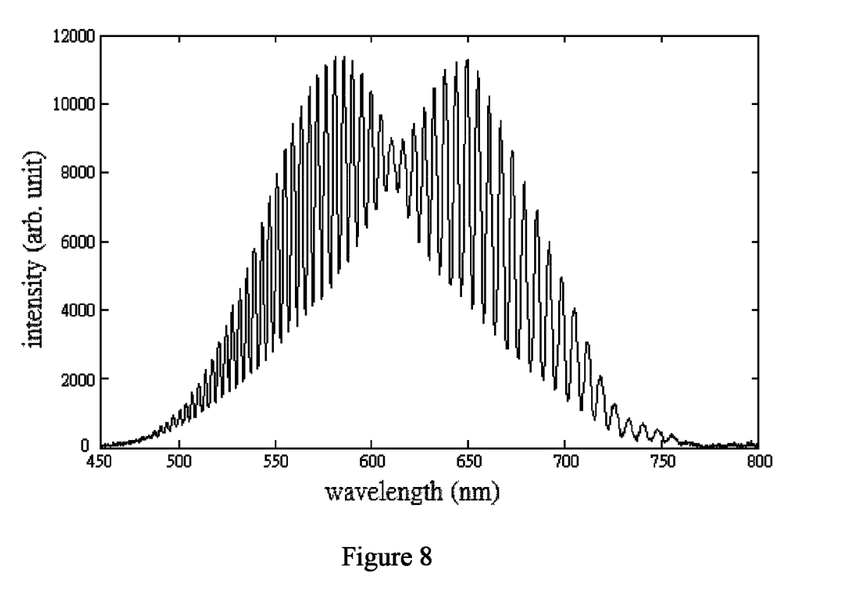
FIG. 8 is a graph illustrating a raw signal of the probe device according to some disclosed embodiments.

As shown in FIG. 4, the reference device 400 may comprise a polarizer 401, a lens 402 and an analyzer 403. In an embodiment, the polarizer 401 may be configured to receive a part (about 5%) of the second light beam to generate a reference light beam. The polarizer 401 may be placed in front of the lens 402 and configured to receive a part of the second light beam to generate a reference light beam. The lens 402 may be configured to couple the reference light beam to the analyzer 403. The analyzer 403 may be configured to extract the reference optical characteristic variation caused by the interference between the p-polarized and s-polarized components of the reference light beam. For example, the polarizer 401 may be set at 45 degree relative to the optical axial of the s-polarization component of the second light beam to generate signal output from the interference between the p- and s-polarization components. An optical intensity variation of the spectral interference pattern can be converted to an electrical signal as shown in FIG. 7.

Figure 5:
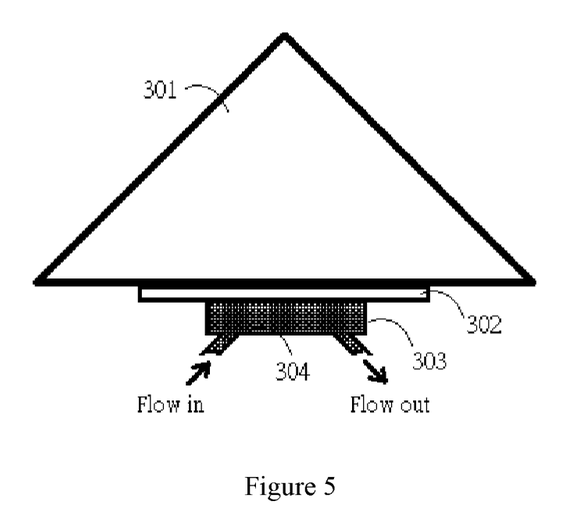
FIG. 5 is a schematic diagram illustrating a SPR sensor consistent with some disclosed embodiments.

Referring to FIG. 5, the SPR sensor 300 may comprise a prism 301, a transducing layer 302 and a sample flow chamber 303. According to an embodiment, the prism 301 may be configured to receive the other part (about 95%) of the second light beam. The prism 301 may be made of transparent dielectric material such as plastic, glass or any other suitable materials in order to match the momentum both in the incoming optical light beam and the surface plasmon wave (SPW) excited on the sensing surface. In this embodiment, a right-triangle prism made of BK7 glass may be employed.

The transducing layer 302 may be coated on a surface of the prism 301 to serve as a sensing surface passed by the received second light beam. In one embodiment, the transducing layer 302 is typically made of a conducting material such as gold or sliver. In this embodiment, a thin layer of gold, about 50 nm, is employed because of its good chemical resistance. The thickness of such a layer is normally at the range of 5 nm to 85 nm depending on the application and the presence of a transducing layer further coated on the metal film. In addition, the transducing layer 302 may be a single layer structure, a multi-layer structure, a grating structure, a patterned structure or any other suitable structure for surface plasmon excitation.

Figure 10:
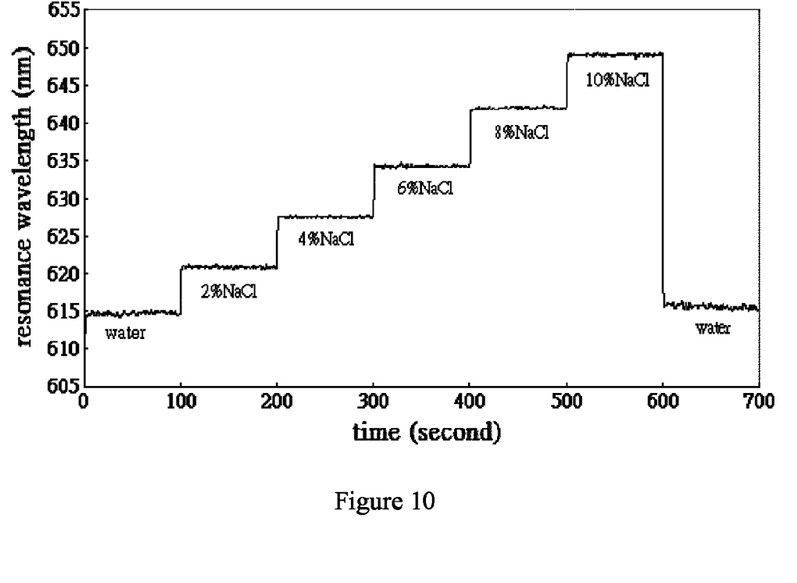
FIG. 10 shows the experimental result of a wide dynamic range spectral phase sensitive SPR sensor obtained from salt and water mixtures.

The sample flow chamber 303 may be provided on the transducing layer to allow a sample 304 flowing through the sensing surface such that the SPR effect associated with the sample is introduced to the passed second light beam. The sample is normally in aqueous or gas form. In this embodiment, NaCl-water mixtures in concentrations of weight percentage from 0% to 10% may be used in order to demonstrate the operation of the scheme. Experimental results, which are recorded as the spectral location of the SPR absorption dips versus time when NaCl-water mixtures of different concentration are sequentially introduced to the sample flow chamber 303 using a syringe pump, are shown in FIG. 10. Since only the p-polarization component of the passing light beam is affected by SPR effect, and the s-polarization component is kept unchanged, any change in phase difference between the p- and s-polarization components is only associated with a shift in the optical properties of the sample, e.g. change in NaCl concentration in the embodiment, which subsequently changes the SPR conditions of the sensing surface.

Back to FIG. 4, the determiner 500 may comprise a polarizer 501, a lens 502, an analyzer 503 and a processing module 504. According to an embodiment, the polarizer 501 may be configured to receive the third light beam to generate a probe light beam. The lens may be placed in the back of the polarizer 501 and configured to couple the probe light beam to the analyzer 503. The analyzer 503 may be configured to extract the probe optical characteristic variation induced by the SPR effect of the probe light beam. The processing module 504 may be configured to determine characteristics of the sample by comparing the reference optical characteristic variation and the probe optical characteristic variation. In another embodiment, the determiner may further comprise a reflective mirror 505 and a variable optical iris 506. The reflective mirror 505 may be configured to change the direction of the received third light beam. The variable optical iris 506 may be configured to confine a field of view of the determiner 500.

Figure 9:
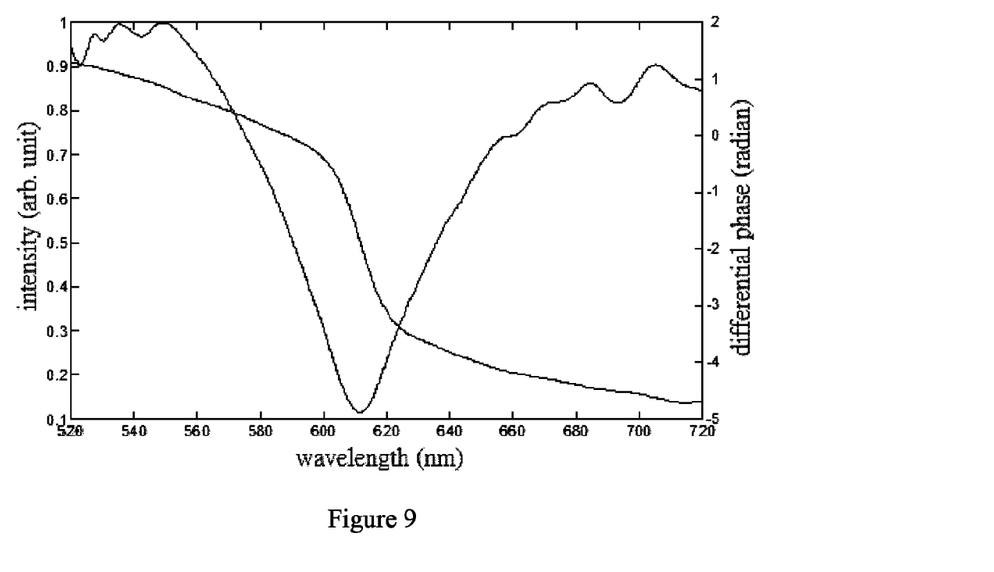
FIG. 9 shows the computed spectral and spectral phase information by comparing the signals of reference device and probe device.

In an embodiment, the analyzer 503 may further comprise an optical grating for splitting light beam into different diffraction angle depending on its wavelengths. Furthermore, the analyzer 503 may further comprise a lens that collects the diffracted light for the optical detection and a linear detector array having a plurality of pixels, with each pixel capturing the light intensity of a specific wavelength. The detector array may be a linear charge-coupled device (CCD) detector array. The signal trace from the optical detector array contains a series of data points representing the intensities of individual wavelengths within the spectral range covering the SPR spectral dip. The processing module 504 may read in the data series and computes the spectral phase and spectral intensity dip associated with the SPR effect taking place in the SPR sensor 300, and also calculates the differential change in spectral distribution and spectral phase using data generated from the reference device 400. FIG. 9 shows a typical SPR spectral dip and spectral phase produced by the processing module 504.

Figure 6:
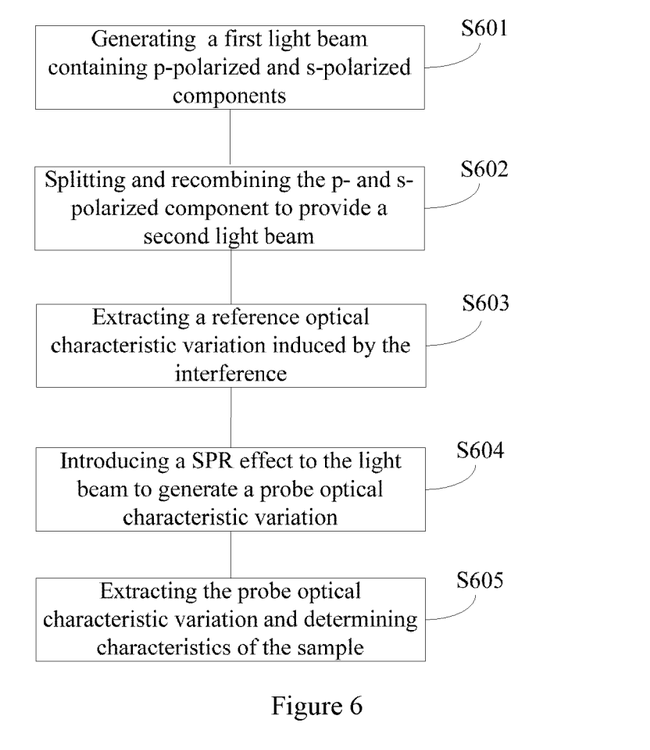
FIG. 6 is a flowchart illustrating a method for detecting characteristics of a sample consistent with some disclosed embodiments.

FIG. 6 is a flowchart illustrating a method for detecting characteristics of a sample consistent with some disclosed embodiments. At step S601, the broadband source 100 generates a first light beam containing p-polarized and s-polarized components. At step S602, the interferometer 200 directs the p-polarized and s-polarized components to a first path and a second path, respectively. The first path has different length from the second path such that the p-polarized and s-polarized components are reflected and then recombined to provide a second light beam with a interference between the p-polarized and s-polarized components. At step S603, the reference device 400 receives a part of the second light beam to extract a reference optical characteristic variation induced by the interference between the p-polarized and s-polarized components of the second light beam. At step S604, the SPR sensor 300 receives the other part of the second light beam and introduces a SPR effect associated with a sample to the second light beam, such that a third light beam with a probe optical characteristic variation induced by the SPR effect is generated. At step S605, the determiner receives the third light beam to extract the probe optical characteristic variation induced by the SPR effect and compares the reference optical characteristic variation and the probe optical characteristic variation in order to determine characteristics of the sample.

The embodiments of the present invention may be implemented using certain hardware, software, or a combination thereof. In addition, the embodiments of the present invention may be adapted to a computer program product embodied on one or more computer readable storage media (comprising but not limited to disk storage, CD-ROM, optical memory and the like) containing computer program codes.

In the foregoing descriptions, various aspects, steps, or components are grouped together in a single embodiment for purposes of illustrations. The disclosure is not to be interpreted as requiring all of the disclosed variations for the claimed subject matter. The following claims are incorporated into this Description of the Exemplary Embodiments, with each claim standing on its own as a separate embodiment of the disclosure.

Moreover, it will be apparent to those skilled in the art from consideration of the specification and practice of the present disclosure that various modifications and variations can be made to the disclosed systems and methods without departing from the scope of the disclosure, as claimed. Thus, it is intended that the specification and examples be considered as exemplary only, with a true scope of the present disclosure being indicated by the following claims and their equivalents.

What is claimed is:

1. An optical sensing apparatus comprising:
a broadband source configured to generate a first light beam containing a p-polarized component and an s-polarized component;
an interferometer configured to direct the p-polarized component and the s-polarized component to a first path and a second path, respectively, wherein the first path has a different length than the second path such that the p-polarized component and the s-polarized component are reflected and then recombined to provide a second light beam with interference between the p-polarized component and the s-polarized component;
a reference device configured to receive a part of the second light beam to extract a reference optical characteristic variation induced by the interference;
a surface plasmon resonance (SPR) sensor configured to receive the other part of the second light beam and to introduce an SPR effect associated with a sample to the second light beam, such that a third light beam with a probe optical characteristic variation induced by the SPR effect is generated;
a polarizer configured to receive the third light beam to generate a probe light beam;
a lens placed in the back of the polarizer and configured to couple the probe light beam to an analyzer, such that the analyzer extracts the probe optical characteristic variation induced by the SPR effect of the probe light beam; and
a processing module configured to determine characteristics of the sample by comparing the reference optical characteristic variation and the probe optical characteristic variation to determine characteristics of the sample.

2. The apparatus according to claim 1, wherein the SPR sensor comprises:
a prism configured to receive the other part of the second light beam;
a transducing layer coated on a surface of the prism to serve as a sensing surface, the received second light beam passing through the sensing surface; and
a sample flow chamber arranged on the transducing layer to allow the sample to flow through the sensing surface such that the SPR effect associated with the sample is introduced to the passed second light beam.

3. The apparatus according to claim 1, wherein the broadband source comprises:
a broadband electromagnetic radiation source configured to emit a broadband light beam containing the p-polarized component and the s-polarized component;
a collimator configured to convert the broadband light beam into a parallel light beam; and
a polarizer configured to select a content ratio between the p-polarized component and the s-polarized component.

4. The apparatus according to claim 3, wherein the broadband source further comprises:
a variable optical iris configured to adjust a beam diameter of the light beam and to restrict an angular field of view of the light beam.

5. The apparatus according to claim 1, wherein the reference device comprises:
a polarizer configured to receive a part of the second light beam to generate a reference light beam;
a lens placed in the back of the polarizer and configured to couple the reference light beam to an analyzer; and
an analyzer configured to extract the reference optical characteristic variation caused by the interference between the p-polarized component and the s-polarized component of the reference light beam.

6. The apparatus according to claim 1, wherein the interferometer comprises:
a broadband polarizing beam splitter configured to split the first light beam into the p-polarized component light beam passing a first path and the s-polarized component light beam passing a second path;
a first quarter chromatic waveplate located in the first path,
a second quarter chromatic waveplate located in the second path, wherein the first quarter chromatic waveplate and second quarter chromatic waveplate are configured to change the polarization of the p-polarized component and the s-polarized component of the passing light beam;
a first reflective unit located in the back of the first quarter chromatic waveplate to reflect the light beam passing the first path;
a second reflective unit located in the back of the second quarter chromatic waveplate to reflect the light beam passing the second path; and
wherein the reflected light beams are recombined by the broadband polarizing beam splitter such that an interference between the p-polarized component and the s-polarized component in the reflected light beams is generated.

7. The apparatus according to claim 1, wherein the interferometer further comprises:
a non-polarizing beam splitter configured to separate the recombined light beam into said part of the second light beam and said the other part of the second light beam.

8. The apparatus according to claim 1, wherein the determiner comprises:
a polarizer configured to receive the third light beam to generate a probe light beam;
a lens placed in the back of the polarizer and configured to couple the probe light beam to an analyzer, such that the analyzer extracts the probe optical characteristic variation induced by the SPR effect of the probe light beam; and
a processing module configured to determine characteristics of the sample by comparing the reference optical characteristic variation and the probe optical characteristic variation.

9. The apparatus according to claim 8, wherein the determiner further comprises a reflective mirror and a variable optical iris, wherein the reflective mirror is configured to direct the received third light beam to the variable optical iris such that the iris confines a field of view of the determiner.

10. The apparatus according to claim 8, wherein the processing module receives the reference optical characteristic variation from the reference device and the probe optical characteristic variation from the analyzer, and determines the refractive index change associated with the sample by comparing the reference optical characteristic variation and the probe optical characteristic variation.

11. The apparatus according to claim 1, wherein the optical characteristic comprises at least one selected from the group consisting of a spectral phase retardation, an optical intensity, and a spectral distribution.

12. The apparatus according to claim 1, wherein the broadband source comprises at least one selected from the group consisting of a tungsten lamp, a halogen lamp, an arc discharge lamp, a white-light emitting diode, a broadband super luminescent diode, and a super continuum laser source.

13. The apparatus according to claim 3, wherein the broadband light beam is generated by cascading a plurality of single electromagnetic radiation sources.

14. The apparatus according to claim 1, wherein the interferometer is a Michelson interferometer or a Mach-Zehnder interferometer.

15. A method for detecting characteristics of a sample, comprising:
    generating, from a broadband source, a first light beam containing a p-polarized component and an s-polarized component;
    directing the p-polarized component and the s-polarized component to a first path and a second path, respectively, wherein the first path has different length from the second path such that the p-polarized component and the s-polarized component are reflected and then recombined to provide a second light beam with a interference between the p-polarized component and s-polarized component;
    extracting a reference optical characteristic variation induced by the interference between the p-polarized component and the s-polarized component of a part of the second light beam;
    introducing a SPR effect associated with a sample to the other part of the second light beam, such that a third light beam with a probe optical characteristic variation induced by the SPR effect is generated;
    extracting the probe optical characteristic variation induced by the SPR effect of the third light beam using:
    a polarizer configured to receive the third light beam to generate a probe light beam and a lens placed in the back of the polarizer and configured to couple the probe light beam to an analyzer, such that the analyzer extracts the probe optical characteristic variation induced by the SPR effect of the probe light beam; and
    a processing module configured to determine characteristics of the sample by comparing the reference optical characteristic variation and the probe optical characteristic variation; and
    comparing the reference optical characteristic variation and the probe optical characteristic variation to determine characteristics of the sample.

16. The method according to claim 15, wherein the introducing comprises:
    receiving, by a prism, the other part of the second light beam;
    coating a transducing layer on a surface of the prism to serve as a sensing surface, the received second light beam passing through the sensing surface; and
    introducing the SPR effect associated with the sample to the passed second light beam by allowing the sample to flow through the sensing surface.

17. The method according to claim 15, wherein the generating comprises:
    emitting a broadband light beam containing the p-polarized component and the s-polarized component;
    converting the broadband light beam into a parallel light beam; and
    selecting a content ratio between the p-polarized component and the s-polarized component.

18. The method according to claim 17, wherein the generating further comprises:
    adjusting a beam diameter of the light beam and to restrict an angular field of view of the light beam.

19. The method according to claim 15, wherein the extracting a reference optical characteristic variation comprises:
    receiving a part of the second light beam to generate a reference light beam;
    coupling the reference light beam to an analyzer; and
    extracting the reference optical characteristic variation caused by the interference between the p-polarized component and the s-polarized component of the reference light beam.

20. The method according to claim 15, wherein the directing comprise:
    splitting the first light beam into the p-polarized light beam passing a first path and the s-polarized component light beam passing a second path;
    changing the polarization of the passing light beam in the first path and the second path;
    reflecting the light beam passing the first path and the second path, respectively; and
    recombining the reflected light beams such that a interference between the p-polarized and s-polarized components is generated.

* * * * *